(12) United States Patent
Olivier et al.

(10) Patent No.: US 9,102,909 B2
(45) Date of Patent: Aug. 11, 2015

(54) MICROBIOLOGICAL ANALYSIS ASSEMBLY AND METHOD

(75) Inventors: Stephane Olivier, Rosheim (FR); Mathieu Arrault, Saverne (FR)

(73) Assignee: EMD Millipore Corporation, Billerica, MA (US)

(*) Notice: Subject to any disclaimer, the term of this patent is extended or adjusted under 35 U.S.C. 154(b) by 347 days.

(21) Appl. No.: 13/088,632

(22) Filed: Apr. 18, 2011

(65) Prior Publication Data

US 2011/0189725 A1    Aug. 4, 2011

Related U.S. Application Data

(62) Division of application No. 12/082,712, filed on Apr. 14, 2008, now Pat. No. 8,642,321.

(30) Foreign Application Priority Data

Apr. 26, 2007    (FR) ..................................... 07 54726

(51) Int. Cl.
 *C12M 1/22*    (2006.01)
 *C12M 1/00*    (2006.01)
 (Continued)

(52) U.S. Cl.
 CPC ................ *C12M 29/04* (2013.01); *C12M 1/12* (2013.01); *C12M 23/26* (2013.01); *C12M 23/32* (2013.01); *C12M 23/42* (2013.01); *C12M 25/14* (2013.01); *C12M 33/14* (2013.01)

(58) Field of Classification Search
 CPC ................................ C12M 33/14; C12M 1/12
 USPC ........................ 435/4, 29, 287.1, 287.9, 305.1
 See application file for complete search history.

(56) References Cited

U.S. PATENT DOCUMENTS

| 2,830,785 A | 4/1958 | Buri |
| 2,923,669 A | 2/1960 | Poitras |

(Continued)

FOREIGN PATENT DOCUMENTS

| EP | 0025350 A2 | 3/1981 |
| EP | 0612850 A2 | 8/1994 |

(Continued)

OTHER PUBLICATIONS

Final Rejection dated Jun. 22, 2011 in corresponding U.S. Appl. No. 12/082,712.

(Continued)

*Primary Examiner* — Jonathan Hurst
(74) *Attorney, Agent, or Firm* — Nields, Lemack & Frame, LLC

(57) ABSTRACT

The assembly comprises a filtration unit and a gel growth medium cassette, the unit and the cassette being adapted to cooperate in order to occupy a nested position in which a membrane covers the gel growth medium, the unit and the cassette each being equipped with an intermediate stop, it being possible for at least one of the two stops to move clear so as to allow the unit to move from an intermediate position, in which the membrane is spaced away from the said gel growth medium, into the nested position. The method comprises selecting such an assembly, of engaging the unit on the cassette until the intermediate stop of the unit comes into contact with the intermediate stop of the cassette, and the step of moving clear the stop able to move clear so as to allow the unit to move from the intermediate position into the nested position.

5 Claims, 7 Drawing Sheets

(51) Int. Cl.
*C12M 1/12* (2006.01)
*C12M 3/00* (2006.01)
*C12M 1/26* (2006.01)

(56) References Cited

U.S. PATENT DOCUMENTS

| | | |
|---|---|---|
| 3,520,660 A | 7/1970 | Hoffman et al. |
| 3,745,090 A | 7/1973 | Chappelle et al. |
| 3,940,250 A | 2/1976 | Plakas et al. |
| 4,283,490 A | 8/1981 | Plakas |
| 4,297,211 A | 10/1981 | Hiesinger et al. |
| 4,521,111 A | 6/1985 | Paulson, Jr. et al. |
| 4,748,124 A | 5/1988 | Vogler |
| 4,868,357 A | 9/1989 | Serikawa et al. |
| 4,912,037 A | 3/1990 | Lemonnier |
| 5,108,768 A | 4/1992 | So |
| 5,202,262 A * | 4/1993 | Lemonnier ............ 435/287.7 |
| 5,288,638 A | 2/1994 | Lemonnier |
| 5,366,867 A | 11/1994 | Kawakami et al. |
| 5,409,829 A | 4/1995 | Mussi et al. |
| 5,693,537 A | 12/1997 | Wilson et al. |
| 5,766,868 A | 6/1998 | Seto |
| 5,783,399 A | 7/1998 | Childs et al. |
| 5,811,251 A | 9/1998 | Hirose et al. |
| 5,891,702 A | 4/1999 | Sakakibara et al. |
| 5,908,751 A | 6/1999 | Higo et al. |
| 6,007,343 A | 12/1999 | O'Brien |
| 6,157,014 A | 12/2000 | Goranson |
| 6,180,405 B1 | 1/2001 | Aitken-Christie et al. |
| 6,346,069 B1 | 2/2002 | Collier |
| 6,358,730 B1 | 3/2002 | Kane |
| 6,642,953 B1 | 11/2003 | Nieto Velasco et al. |
| 6,776,294 B2 | 8/2004 | Lemonnier |
| 7,806,274 B2 | 10/2010 | Scott et al. |
| 8,064,661 B2 | 11/2011 | Komori et al. |
| 8,642,321 B2 | 2/2014 | Olivier et al. |
| 2002/0192739 A1 | 12/2002 | Lemonnier |
| 2003/0096322 A1 | 5/2003 | Giuliano et al. |
| 2004/0009098 A1 | 1/2004 | Torre-Bueno |
| 2004/0009473 A1 | 1/2004 | Pease |
| 2004/0110273 A1 | 6/2004 | Akers et al. |
| 2004/0197845 A1 | 10/2004 | Hassibi et al. |
| 2004/0241785 A1 | 12/2004 | Schann et al. |
| 2005/0069973 A1 | 3/2005 | Bashar et al. |
| 2005/0129582 A1 | 6/2005 | Breidford et al. |
| 2005/0136506 A1 | 6/2005 | Kamath |
| 2005/0153387 A1 | 7/2005 | Lehmann et al. |
| 2005/0221403 A1 | 10/2005 | Gazenko |
| 2006/0008860 A1 | 1/2006 | Fan et al. |
| 2007/0207514 A1 | 9/2007 | Grinon et al. |
| 2007/0212750 A1 | 9/2007 | Kieffer et al. |
| 2007/0231844 A1 | 10/2007 | Grinon et al. |
| 2007/0231845 A1 | 10/2007 | Grinon et al. |
| 2008/0268422 A1 | 10/2008 | Olivier et al. |
| 2010/0173335 A1 | 7/2010 | Grinon et al. |

FOREIGN PATENT DOCUMENTS

| | | |
|---|---|---|
| EP | 0529084 B1 | 5/1997 |
| EP | 0781851 A2 | 7/1997 |
| EP | 0803577 A2 | 10/1997 |
| EP | 0974827 A2 | 1/2000 |
| EP | 1067199 A1 | 1/2001 |
| FR | 2677664 A1 | 12/1992 |
| FR | 2802942 A1 | 6/2001 |
| FR | 2830872 A1 | 4/2003 |
| JP | 6-78748 A | 3/1994 |
| JP | 6-237793 A | 8/1994 |
| JP | 2517102 B2 | 7/1996 |
| JP | 9-182600 A | 7/1997 |
| JP | 10-28599 A | 2/1998 |
| JP | 11-32792 A | 2/1999 |
| JP | 3133328 B2 | 11/2000 |
| JP | 2001-91466 A | 4/2001 |
| JP | 2005-528907 A | 9/2005 |
| WO | 03/104383 A1 | 12/2003 |
| WO | 2004/009840 A1 | 1/2004 |
| WO | 2006/051813 A1 | 5/2006 |

OTHER PUBLICATIONS

Office Action mailed Mar. 30, 2012 in corresponding U.S. Appl. No. 12/082,712.
Chinese Communication dated Dec. 19, 2008, with English translation, in co-pending foreign application No. 20710085858.2.
European Communication dated Jun. 1, 2007 in co-pending foreign application No. EP 07290214.1.
European Communication dated Sep. 15, 2008 in corresponding foreign application No. EP 08290298.2.
French Search Report dated Oct. 11, 2006 in co-pending foreign application No. FR 0650645.
French Search Report dated Oct. 11, 2006 in co-pending foreign application No. FR 0650644.
French Search Report dated Sep. 27, 2006 in co-pending foreign application No. FR 0650646.
French Search Report dated Nov. 15, 2006 in co-pending foreign application No. FR 0650647.
French Search Report dated Sep. 26, 2007 in corresponding foreign application No. FR 0754726.
Japanese communication, with English translation, dated Dec. 15, 2009 in co-pending foreign application No. JP 2007-037424.
Jpanese communication, with English translation, dated Dec. 15, 2009 in co-pending foreign application No. JP 2007-037425.
Office Action dated Aug. 10, 2009 in co-pending U.S. Appl. No. 11/704,831.
Final Rejection dated Dec. 4, 2009 in co-pending U.S. Appl. No. 11/704,831.
Final Rejection dated Feb. 22, 2010 in co-pending U.S. Appl. No. 11/704,831.
Final Rejection dated Jul. 1, 2010 in co-pending U.S. Appl. No. 11/704,831.
Office Action dated Aug. 11, 2009 in co-pending U.S. Appl. No. 11/704,812.
Final Rejection dated Feb. 16, 2010 in co-pending U.S. Appl. No. 11/704,812.
Final Rejection dated Jun. 9, 2010 in co-pending U.S. Appl. No. 11/704,812.
Office Action dated Oct. 19, 2010 in co-pending U.S. Appl. No. 11/704,812.
Office Action dated Sep. 30, 2009 in co-pending U.S. Appl. No. 11/704,867.
Final Rejection dated May 24, 2010 in co-pending U.S. Appl. No. 11/704,867.
Office Action dated May 25, 2010 in co-pending U.S. Appl. No. 11/727,273.
Final Rejection dated Nov. 22, 2010 in co-pending U.S. Appl. No. 11/727,273.
Office Action dated Oct. 6, 2009 in co-pending U.S. Appl. No. 11/704,777.
Final Rejection dated Jul. 7, 2010 in co-pending U.S. Appl. No. 11/704,777.
Office Action dated Oct. 14, 2010 in corresponding U.S. Appl. No. 12/082,712.
Office Action mailed Jun. 20, 2013 in corresponding U.S. Appl. No. 12/082,712.
Office Action mailed Jan. 9, 2014 in corresponding U.S. Appl. No. 11/704,777.
Notice of Allowance mailed Nov. 6, 2013 in corresponding U.S. Appl. No. 12/082,712.
Office Action mailed Jan. 29, 2013 in corresponding U.S. Appl. No. 11/704,867.
Final Rejection mailed Dec. 18, 2012 in corresponding U.S. Appl. No. 12/082,712.
Office Action mailed May 15, 2013 in corresponding U.S. Appl. No. 11/704,777.
Office Action mailed Mar. 30, 2015 in corresponding U.S. Appl. No. 11/704,777.
Final Rejection mailed Aug. 19, 2014 in co-pending U.S. Appl. No. 11/704,777.

* cited by examiner

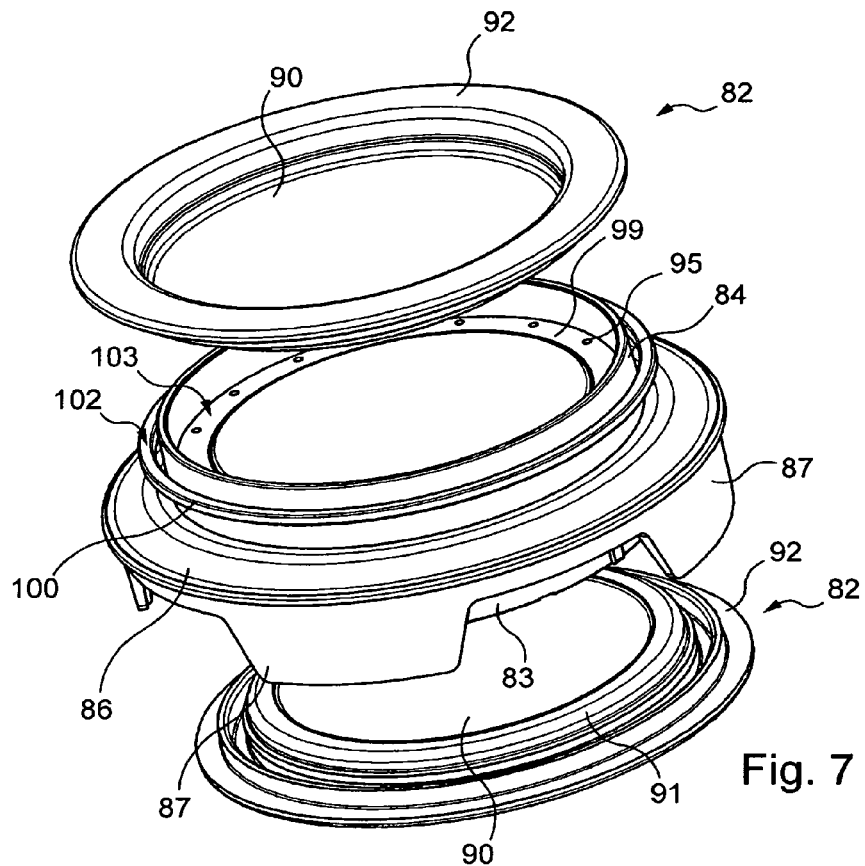
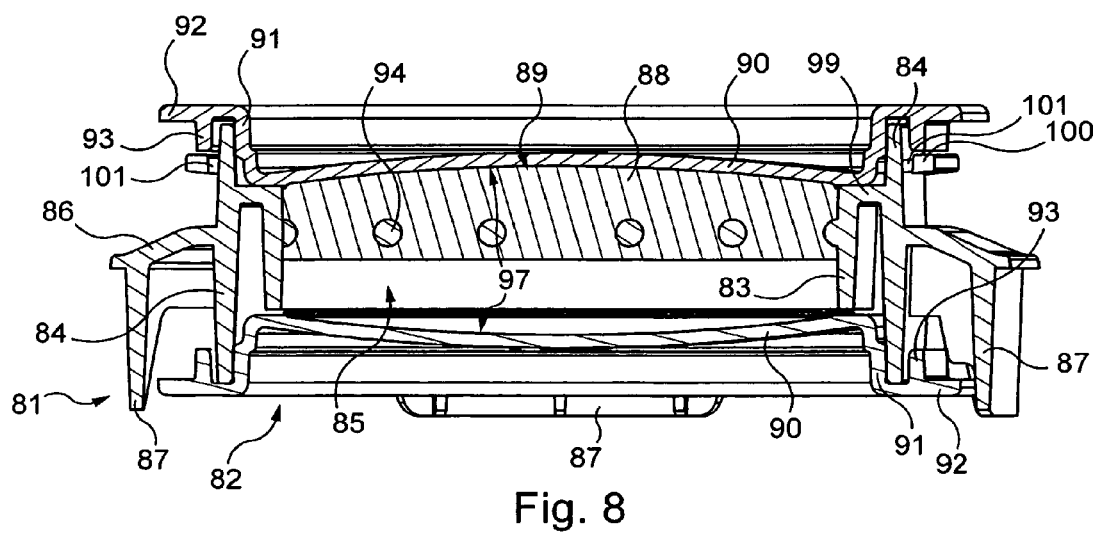

MICROBIOLOGICAL ANALYSIS ASSEMBLY AND METHOD

This application is a divisional of U.S. patent application Ser. No. 12/082,712, filed Apr. 14, 2008, now U.S. Pat. No. 8,642,321, the disclosure of which is incorporated herein by reference.

BACKGROUND

The present invention relates to the microbiological analysis of a sample of liquid in a pressurized flow.

Units for the microbiological testing of samples of pressurized liquid comprising a microporous membrane through which the liquid is filtered under pressure are already known, particularly from French patent 2 802 942.

Such units comprise a body for admitting the liquid that is to be filtered and a body for draining this liquid away, the admission and drainage bodies of this unit being locked together one on each side of the filter membrane, sandwiching this membrane over an annular area with the interposition of a seal.

Locking is achieved by means of frangible latching tabs which are broken after filtration in order to disconnect the two bodies and thus gain access to the membrane, it then being possible for this membrane to be gripped in forceps via its edge to be set down on the top surface of gel growth medium poured beforehand into a growing cassette such as a petri dish for example.

SUMMARY

The invention aims to provide a microbiological analysis assembly which is similar but at the same time simpler and more reliable to handle (reducing the risks of detecting false positives) while at the same time optimizing performance in respect of the growing of any micro-organisms that may have been collected on the membrane (reducing the risks of detecting false negatives).

To this end the invention provides a microbiological analysis assembly comprising a filtration unit and a gel growth medium cassette, the said filtration unit comprising a filter membrane and a body with which the said membrane is associated, the said cassette comprising a body containing the said gel growth medium, the latter having a surface designed to be covered by the said membrane, characterized in that the body of the filtration unit and the body of the cassette are adapted to cooperate in order to occupy a nested position in which the membrane covers the said surface of the said gel growth medium, the body of the said unit and the body of the said cassette each being equipped with an intermediate stop with, when the said stops are in contact with one another, the filtration unit and the gel growth medium cassette being in an intermediate position in which the said membrane is spaced away from the said gel growth medium, it being possible for at least one of the two stops to move clear so as to allow the said filtration unit to move from the said intermediate position into the said nested position.

Placing the filtration unit on the cassette in an intermediate position increases the repeatability of the actions performed by the operator thereby ensuring that the unit is pre-positioned and centered on the cassette before the membrane is applied to the gel growth medium, thus making the operator's work simpler and more reliable.

The presence of a stop able to move clear ensures that the membrane is placed in uniform contact with the gel growth medium when the stop moves clear, thus significantly minimizing the risks that air pockets will form between the membrane and the gel growth medium, since such pockets can locally inhibit the growth of the micro-organisms present on the membrane and thus cause false negatives.

In addition, an assembly such as this means that there is no need to separate the membrane from the filtration unit. After filtration, the operator comes into contact merely with the body of the filtration unit without ever having to handle the membrane, using forceps for example, as was done in the assembly of the aforementioned prior art, thus significantly minimizing the risks of contamination.

By virtue of the assembly according to the invention, the combined optimization and simplification of the operations involved in transferring the membrane onto the gel growth medium cassette then in applying this membrane to the gel growth medium thus allow a reduction in the risks of incorrect microbiological analysis, whether in terms of the detection of false positives or in terms of the detection of false negatives.

According to some preferred features, for reasons of simplicity and convenience both in terms of manufacture and in terms of use:
- the said stop able to move clear is adapted to move clear when the force with which the unit and the cassette are brought closer together exceeds a predetermined threshold;
- the said stop able to move clear belongs to the said cassette;
- the said stop able to move clear is connected to a wall of the said body of the cassette by at least one frangible portion;
- the said stop able to move clear is an annular ring;
- the said unit comprises a flexible wall closing a chamber which is further bounded by a wall of the body of the filtration unit and by the said membrane;
- the said flexible wall belongs to a lid nested into the body of the said unit;
- the said body of the filtration unit also comprises retaining means for holding the said unit in the position in which it is nested with the said cassette;
- the intermediate stop of the body of the said unit is a tubular wall that the said body comprises;
- the body of the unit and the body of the cassette are also each equipped with an end-of-travel stop, the said end-of-travel stops being in contact with one another in the said nested position;
- the end-of-travel stop of the body of the filtration unit is an internal wall surrounded by the wall that forms the said intermediate stop;
- the said membrane is sealed against the said internal wall;
- the said end-of-travel stop of the cassette is a wall lying at the periphery of the said gel growth medium;
- the said cassette comprises a tubular wall from which there extend, transversely to it, the said intermediate stop from a first side of the said wall, and the said end-of-travel stop from a second side of the said wall; and/or
- the said gel growth medium has a domed shape, the said surface of the gel growth medium that is designed to be covered by the said membrane being convex.

The invention, in a second aspect, is also aimed at a method, characterized in that it comprises the steps of:
- selecting an analysis assembly as explained hereinabove;
- engaging the said unit on the said cassette until the intermediate stop of the body of the said unit comes into contact with the intermediate stop of the body of the said cassette; and
- moving clear the said stop able to move clear so as to allow the said unit to move from the said intermediate position into the said nested position.

According to some preferred features, for reasons of simplicity and convenience both in terms of manufacture and in terms of use:

a unit comprising a flexible wall closing a chamber further bounded by a wall of the body of the filtration unit and by the said membrane is selected as said filtration unit, the step of moving clear the said stop able to move clear comprising the step of exerting a force to bring the said unit and the said cassette closer together that is above a predetermined threshold, by pressing on the said flexible wall of the said unit;

a wall adapted to deform under a force that is lower than the force required to move clear the said stop is selected as said flexible wall;

the said method comprises, prior to the step of engaging the said unit on the said cassette, a sampling step and, subsequent to the step of moving clear the said stop, a step of growing the micro-organisms collected on the said membrane during the said sampling step; and/or the said sampling step comprises the steps of:
  selecting a filtration unit which comprises a peelable film;
  filtering a predetermined volume of liquid through the said unit; and
  peeling the said film.

The features and advantages of the invention will become apparent from the description which follows, which is given by way of a preferred, although non-limiting, example, with reference to the attached drawings in which:

BRIEF DESCRIPTION OF THE DRAWINGS

FIG. 7 is a view similar to FIG. 6 but showing this cassette in an exploded view;

FIG. 8 is a side view of this cassette cross-sectioned along a central plane of symmetry;

DETAILED DESCRIPTION

Figure 1:
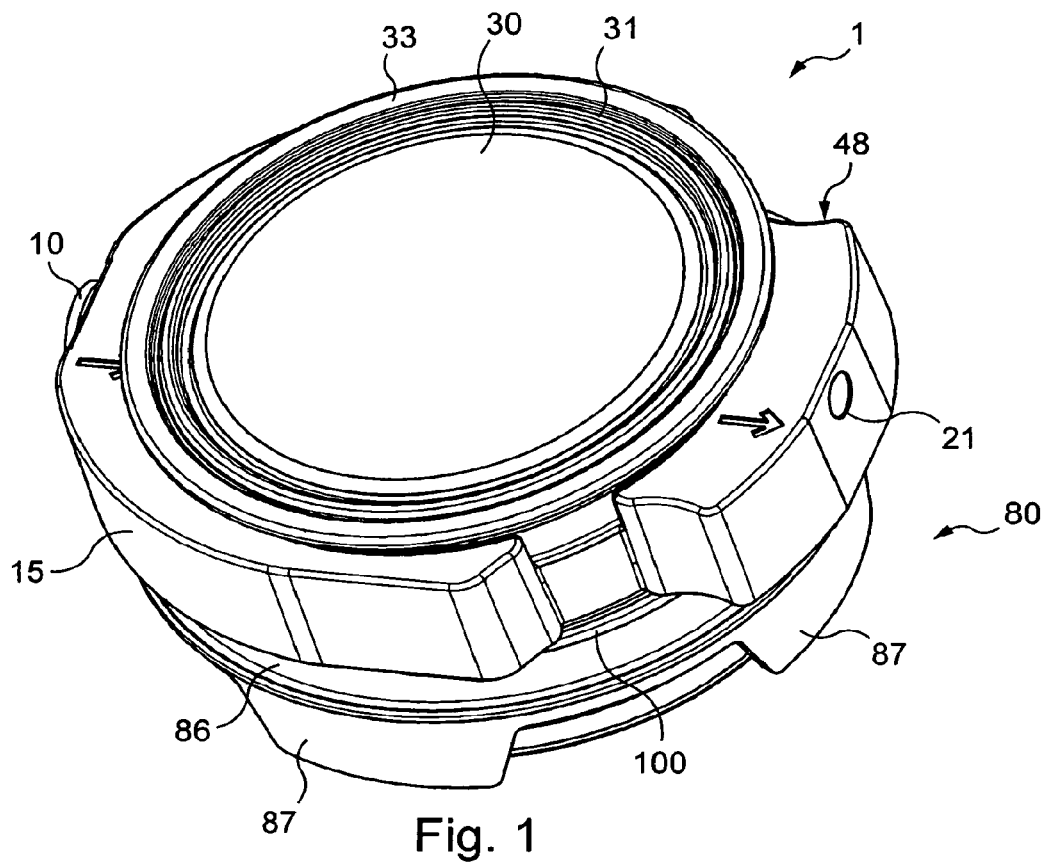
FIG. 1 is a perspective view of an assembly according to the invention, in which a filtration unit equipped with a filter membrane and a gel growth medium cassette that this assembly comprises are depicted in the position in which one is nested inside the other.
Figure 2:
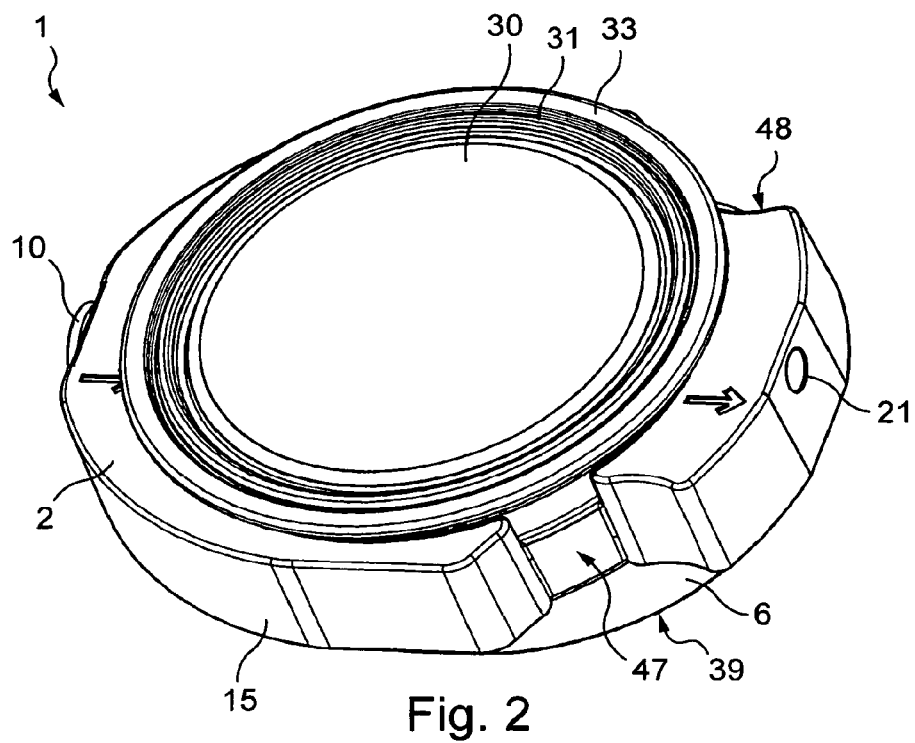
FIG. 2 is a view similar to FIG. 1, but separately showing the filtration unit that this assembly comprises before a protective film that protects the filter membrane has been peeled off this unit.

The microbiological test unit 1 depicted in FIGS. 1 to 4 comprises a body 2, a membrane 3, a porous frit 4, a disk-shaped sponge 5, a peelable plastic film 6 and a lid 7.

The unit also comprises two duckbill check valves 8 and 9 and a female insert 10.

Figure 5:
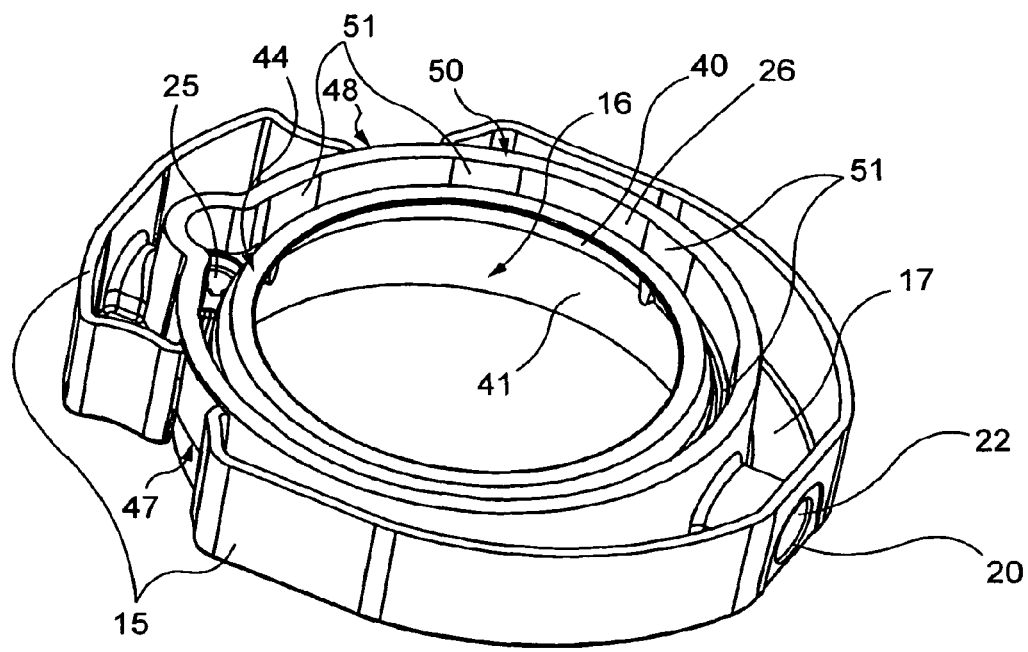
FIG. 5 is a perspective view showing separately a body that this filtration unit comprises, viewed from the side where the membrane is sealed to this body.

The body 2 is made of polycarbonate and produced by molding as a single piece. This body, shown separately in FIG. 5, comprises an external wall 15, interrupted at indentations 47, 48, a frustoconical internal wall 16 converging toward the membrane 3, an annular transverse wall 17 and an intermediate wall 26 positioned between the walls 15 and 16, the walls 16 and 26 meeting at the wall 17.

The walls 15 and 16 are connected to one another by the wall 17.

Figure 4:
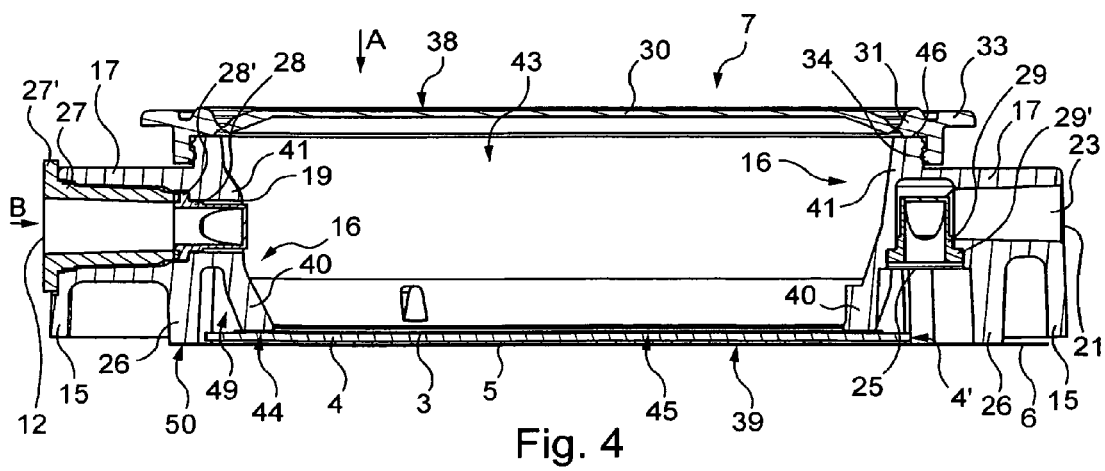
FIG. 4 is a side view of this unit cross-sectioned along a central plane of symmetry.

The wall 16 has an aperture 19 formed between the larger-diameter portion 41 of this wall 16 and the smaller-diameter portion 40 of this wall 16 (FIG. 4).

The aperture 19 is positioned at the end of a duct 22 (FIG. 3), this duct opening to the outside of the unit, at the opposite end to the aperture 19, via an aperture 20 formed in the wall 15.

Diametrically opposite this aperture 20 a second aperture 21 (FIG. 4) is also formed in the wall 15, this second aperture lying at the end of a duct 23. The duct 23 has an elbowed portion which means that it emerges, at the opposite end to the aperture 21, in the space between the walls 16 and 26 via an aperture 25.

The valve 8 is nested inside the duct 22 at the wall 16 centered around its flange 28 and butting against the body 2 via its flange 28'.

In the same way, the valve 9 is nested in the duct 23, the valve being centered about its flange 29, the flange 29' of this valve butting against the wall portion that surrounds the aperture 25.

The valves 8 and 9 are calibrated to open only above a certain pressure threshold when a fluid is applied under pressure in the direction of flow from the inlet aperture 20 toward the outlet aperture 21, and to remain closed otherwise.

Once the valve 8 has been inserted, the insert 10 is also nested into the length of duct 22 on the aperture 20 side, centered about its flange 27, the annular flange 27' of this insert butting against the external surface of the cylindrical wall 15 so that the aperture 12 of this insert, at the opposite end to the valve 8, lies near the aperture 20 of the body 2.

The insert 10 in this instance is a female Luer tip, sealing between this tip and the body 2 being obtained by an ultrasound weld performed around the periphery of this insert.

As in the case of the insert 10, the duct 23 and the walls surrounding it also form a female Luer tip.

The apertures 12 and 21 are each covered by a peelable strip of flexible plastic (not depicted) so as to ensure the integrity of the ducts 22 and 23 by protecting them from the air which is a potential source of microbiological contamination.

Forcibly nested on the same side as the portion 41 of the frustoconical wall 16 is a flexible plastic lid 7.

The body 2 also comprises a pointed annular rib on the edge face of the frustoconical portion 41 that faces toward the outside of the unit and is adapted to seal against this lid, while the wall 26 has eight facets 51 adapted, as will be seen hereinafter, to hold the filtration unit and the gel growth medium cassette in their nested position.

The lid 7 is made of polypropylene and has a obturating wall 30, an annular hinge 31, a cylindrical nesting band 32 and an annular flange 33.

The obturating wall 30 is connected by the annular hinge 31 to the cylindrical nesting band 32 and the flange 33.

In its position in which it is nested against the frustoconical wall 41, the cylindrical band 32 bears against the external surface of this portion via an annular sealing rib 34.

The annular hinge 31 has thinner portions adapted to make it easier to deform the lid.

The membrane 3, which has a diameter of 55 mm, is made of cellulose ester (it may equally be made of polycarbonate or PVDF). This material in particular makes it possible to obtain a microporosity that allows liquids to pass through while at the same time retaining the various micro-organisms they contain.

This membrane is sealed at its periphery against the surface 44 of the wall portion 40, this portion forming an annular rim.

Figure 3:
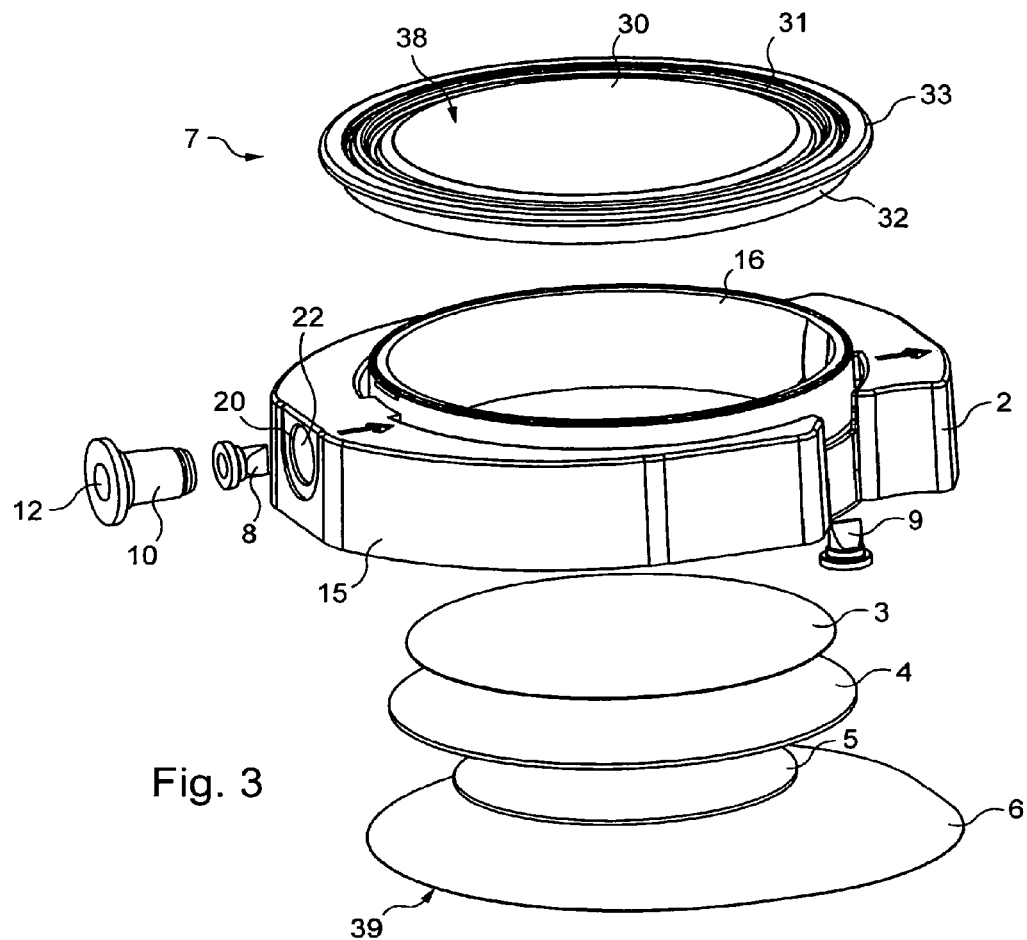
FIG. 3 is a view similar to FIG. 2, but showing this unit in an exploded view.

Positioned under this membrane is the disk-shaped porous frit 4 which has a diameter larger than that of the membrane, so that it is positioned against the portion 40, extending beyond this portion and supporting the membrane over its entire surface (FIGS. 3 and 4).

Positioned under this frit is the disk-shaped sponge 5 which is centered relative to the frit.

The porous frit 4 is supported, via the sponge 5, by a polyethylene film 6 sealed against the surface 50 of the cylindrical wall 26, so that this film hermetically and completely covers the sponge 5, the porous frit 4 and the membrane 3 while at the same time ensuring that the frit 4 is held in position against the membrane 3 and the wall portion 40 via the sponge 5.

This film is sealed to the frit 4 along several bands (not visible in the figures) so as to ensure that this film, this frit and the sponge positioned between them are held together.

The test unit, ready for use (with the lid 7 nested into the body 2 and the film 6 sealed to this body) therefore has two flexible and detachable transverse walls (the wall 30 associated with the hinge and the film 6) which are on the whole mutually parallel, closing the top and the bottom of the filtration chamber bounded by the body 2, the wall 30 (or the film 6) having a face 38 (or 39) facing toward the outside of the unit.

The wall 30 and the film 6 are held in place by simple adhesion phenomena (by friction of the forcible engagement in respect of the wall 30, by virtue of the band 32 and the rib 34, and by sealing or hermetic bonding in the case of the film 6).

More specifically, and as will be seen hereinafter, the lid 7 closes a reception volume 43 for the liquid which lies between the membrane 3, the frustoconical wall 16 and this lid, while the plastic film 6, together with the membrane 3, partially bounds a drainage volume 45 for draining this liquid, which lies under the membrane and includes the space between this membrane and the film 6. This volume communicates with the annular volume 49 located between the wall portion 40 and the wall 26, through which, as will be seen hereinafter, the liquid passes (after having been received in the reception volume 43 then drained into the drainage volume 45) so that this liquid is guided toward the outlet aperture 21 via the duct 23.

This unit, pre-sterilized using gamma radiation, is packaged in a plastic sachet (not depicted) consisting of two thermoplastic sheets joined together by a weld bead, a length of this weld bead being peelable by hand.

Figure 6:
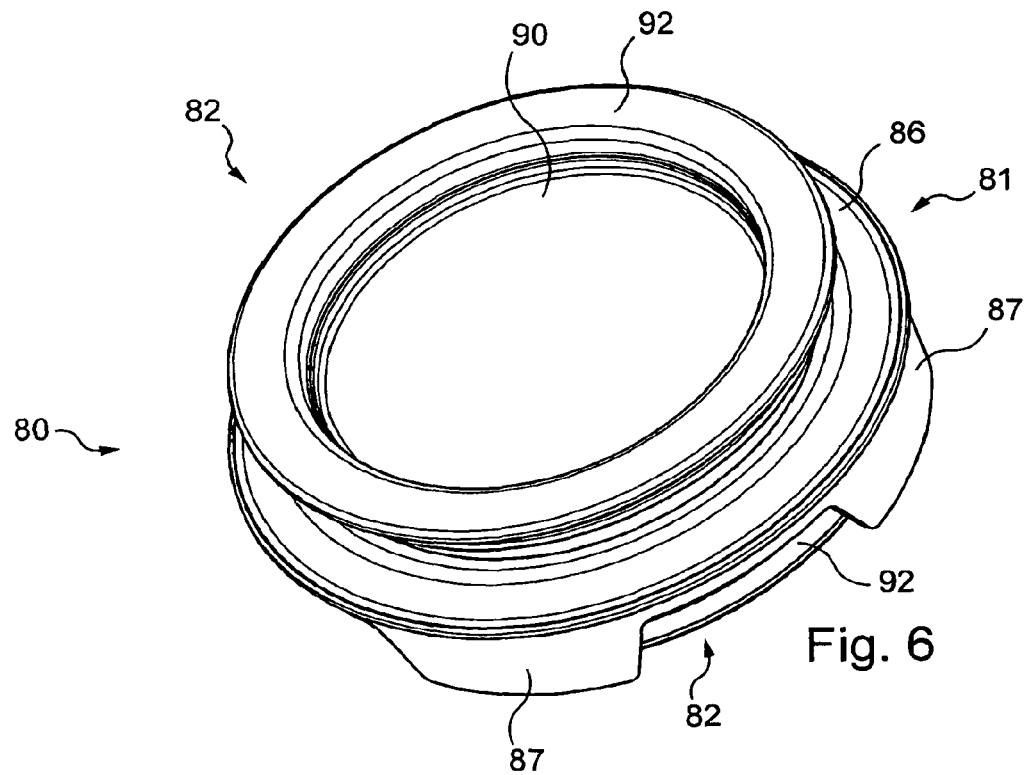
FIG. 6 is a view similar to FIG. 1 but showing separately the gel growth medium cassette that this assembly comprises, and into which an additional lid covering the gel growth medium is nested.

The gel growth medium cassette 80 will now be described with reference to FIGS. 6 to 8.

The gel growth medium cassette 80 has a cassette body 81 and two identical lids 82. The body 81 is of cylindrical overall shape and has a first cylindrical wall 83, a second cylindrical wall 84, a meshed plate 85, a balcony 86 and several teeth 87.

The wall 84 surrounds the wall 83 and is connected to it by a transverse wall 99.

Extending transversely from the wall 84 on the opposite side to the wall 99 is a ring 100 connected to this wall by four uniformly spaced frangible tabs 101.

The mesh 85 is made up of a series of bars 94 which extend from the surface of the wall 83 facing toward the inside of the cassette toward the geometric center of this cylindrical wall, these rods being connected to one another by circular ribs (not visible) so as to form this mesh.

The balcony 86 is connected to the wall 84 on the opposite side to the wall 99. This balcony has a series of uniformly spaced teeth 87 projecting parallel to the wall 84.

The lids 82 each have a domed wall 90 connected by a cylindrical band 91 to a flange 92.

The flange 92 has an annular rib 93 projecting from the same side as the band 91.

An agar-based gel growth medium 88 is poured onto the mesh 85 of the cassette 60 (which at that point is in an inverted position by comparison with the position shown in FIG. 8, the stopper 82 located near the teeth 87 having been removed beforehand) so as to cover this mesh and present, in the direction of the lid 82 which has not yet been removed, a convex surface 89 designed to be covered by the membrane 3.

Each lid 82 of a ready-to-use gel growth medium cassette (FIG. 12) is nested against a respective free edge of the wall 84 (these edges then being positioned between the band 91 and the rib 93 of the corresponding lid 82) so that the concave surfaces 97 of the lids face toward the meshed support 85, the domed wall 90 of the lid 82 closest to the gel growth medium hugging with its concave surface 97 the convex surface 89 of the gel growth medium, thus protecting it from the air.

The wall 99 has several apertures 95 forming vents to prevent the gel growth medium 88 from acting like a suction cup on this lid 82 when the lid is removed.

The gel growth medium cassette is also designed, in order to simplify storage, to allow it to nest together with other identical gel growth medium cassettes, the top lid of the dish of gel growth medium below resting against the bottom lid of the dish of gel growth medium above, the free edges of the teeth 87 of the dish above partially surrounding these two lids to prevent any slippage of one cassette relative to another.

The way in which a microbiological test is performed using a unit and a cassette according to the invention will now be described.

First of all the operator performs a sampling step, that is to say takes a sample for analysis (here a membrane likely to contain micro-organisms).

To do that, the operator opens the individual sachet (by parting the two thermoplastic sheets at the peelable weld bead) in which a unit 1 is contained, in order to extract it therefrom by grasping it at the indentations 47 and 48 of the body 2.

The unit is then engaged in a clamp (not depicted) having two jaws against which the lid 7 and the film 6 rest, to allow them to withstand the pressure of the flowing liquid.

Once the unit is clamped in place using the clamp, the operator peels off the plastic film (not depicted) that obturates the inlet aperture 12 of the unit and then connects the inlet female Luer tip 10 of the unit to a male Luer tip (not depicted)

connected to a filling pipe communicating via a tap (not depicted) with a reservoir (not depicted) of pressurized liquid.

The operator then peels off the plastic film covering the outlet aperture 21 so as to connect the outlet female Luer tip to a drain pipe (not depicted).

The operator then operates the tap to bring the filtration chamber to the same pressure as the liquid, for example 3 bar.

The liquid then passes along the duct 22 in the direction of the arrow B (FIG. 4), the pressure being high enough to open the leaves of the valve 8, then fills the reception volume 43 and begins to pass through the membrane 3 over its entire thickness in the axial direction of filtration depicted by the arrow A (FIG. 4).

Since this membrane is hermetically sealed against the surface 44 of the wall 40, the liquid can escape from the reception volume 43 only by passing right through the entire thickness of the membrane 3.

Once this liquid has been filtered through the membrane, it enters the drainage volume 45 within the porous frit 4 and crosses it at least partially.

Most of the liquid crosses only part of the thickness of the frit, escaping from this frit along its edge face 4' (FIG. 4).

The drainage volume is thus essentially located in the volume occupied by the frit 4 and in the volume running radially (transversely with respect to the axial direction of filtration) around this frit situated near the edge face 4'.

The liquid then travels from the drainage volume 45 toward the transit volume 49 that lies between the wall 40 and the wall 26, distributed around the membrane 3, so that the liquid is led as far as the valve 9.

The leaves of this valve, like those of the valve 8, are designed to open at the operating pressures of the unit, it thus being possible for the liquid to be removed via the aperture 21, passing along the duct 23.

Should the operator mistakenly confuse the inlet and outlet apertures, the check valves 8 and 9 prevent the liquid from passing through the unit in the direction which would, at the membrane 3, lead to a pressure difference that would deform the membrane away from its supporting frit and possibly tear it.

Once all the liquid has been filtered, the operator closes the liquid inlet tap, disconnects the filling and drain pipes from the unit 1 and extracts the unit 1 from the clamp. When the unit has been extracted from this clamp, the water-laden membrane 3 is supported by the frit 4 to prevent it from tearing.

The operator then purges the liquid contained in the unit from this unit by connecting its outlet aperture 21 to a vacuum pump so that this liquid can be withdrawn by suction through the duct 23.

When most of the liquid has been removed, the surfaces of the membrane come into contact with the air that has entered the device.

The bubble point phenomenon means that no gas bubble can leave the wetted membrane and this means that this membrane is sealed against the air, thus preventing any liquid or gas from flowing toward the outlet aperture 21.

In response to this suction the pressure external to the device therefore causes the peelable film 6 to deform, and this film tends to move closer toward the porous frit 4 and the membrane 3.

As a result, the peelable film 6 thus deformed presses the disk-shaped sponge 5 against the frit 4, which means that this sponge thus pressed by the film 6 becomes partially emptied of the liquid it absorbed during filtration.

Once this sponge has been pressed, suction is stopped. A vent (not depicted) at the edge of the valve 9 of the device allows a sterile stream of air in, thus allowing the pressure inside the spaces 45 and 49 to gradually return to a state where they balance the external pressure, so that the film 6 returns to its initial position and the sponge 5, which is relatively elastic and relieved (in the absence of the suction) of the force exerted by the peelable film 6, substantially regains its initial volume without being saturated with water because some of the water it used to contain was removed while it was being pressed.

As a result, when the sponge 5 regains its volume it at the same time absorbs any remaining liquid still contained in the device, especially the liquid still present in the pores of the membrane 3 and in the regions neighboring the preferred flow paths.

Once this purging operation has been performed, the operator grasps the peelable film 6 in the region of the film lying near one of the indentations 47 or 48 (FIG. 2) and removes this film by peeling it off, the block 5 and the porous frit 4 then being pulled away with the film 6 and removed with it (since the film is sealed to the frit at several points), leaving only the membrane 3 secured to the wall 40.

The operation of assembling the filtration unit 1 with the gel growth medium cassette 80 will now be described with reference to FIGS. 9 to 14.

First of all the operator removes the lid 82 protecting the gel growth medium 88 by grasping the flange 92 of this lid to disengage it from the wall 84 (FIG. 13) in order thus to access the surface 89 of the gel growth medium.

Figure 9:
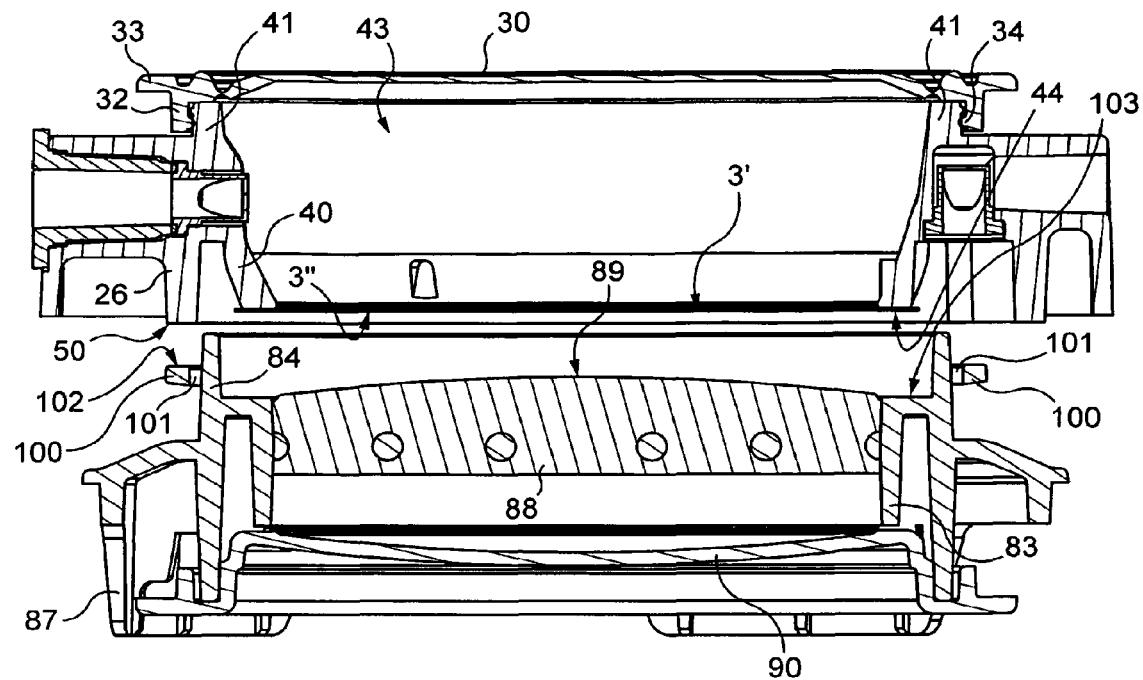
FIGS. 9 to 12 are four sectioned side views respectively illustrating: the step of bringing the filtration unit toward the gel growth medium cassette; the intermediate step of centering this unit on the cassette; the step of deforming a flexible wall that a lid of the filtration unit comprises prior to moving clear a frangible ring that the cassette comprises; and the step of covering the gel growth medium with the membrane after this ring has been moved clear.

The operator, having thus uncovered the surfaces 3" of the membrane and 89 of the gel growth medium that are to be brought into contact with one another, positions the filtration unit over the cassette as illustrated in FIG. 9 in order to engage the body of the unit on that of the cassette.

Figure 10:
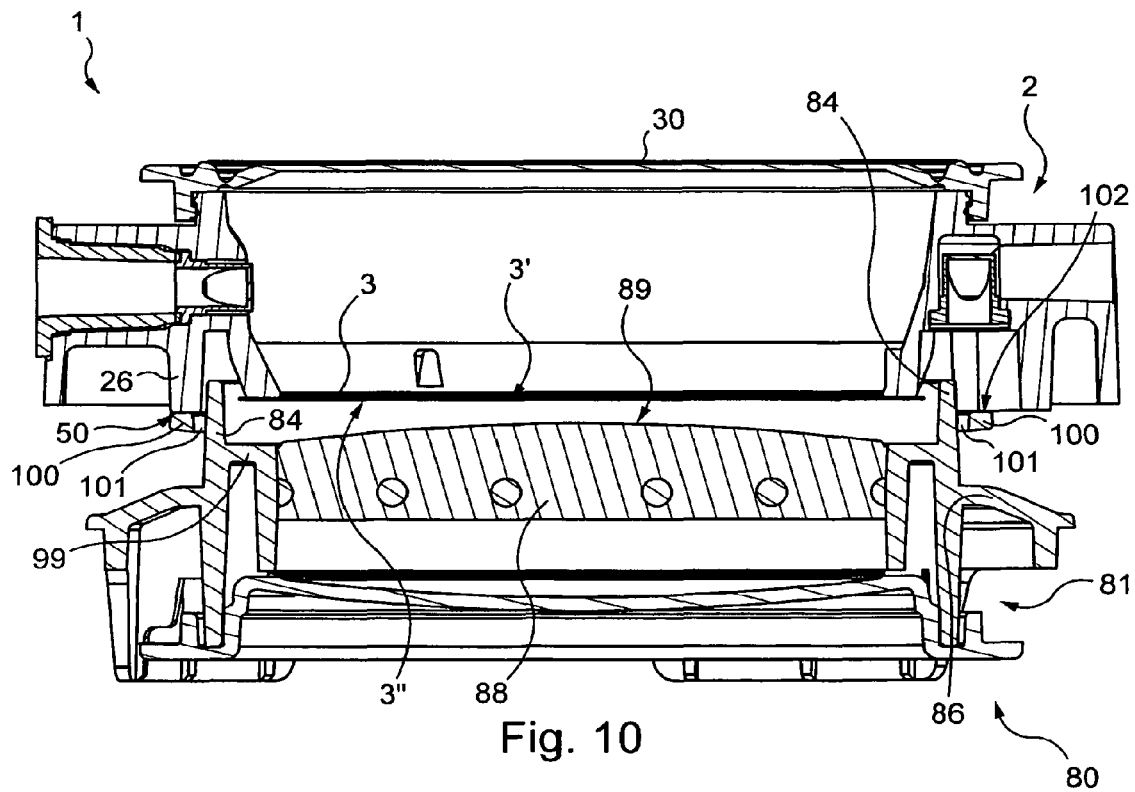
Figure 13:
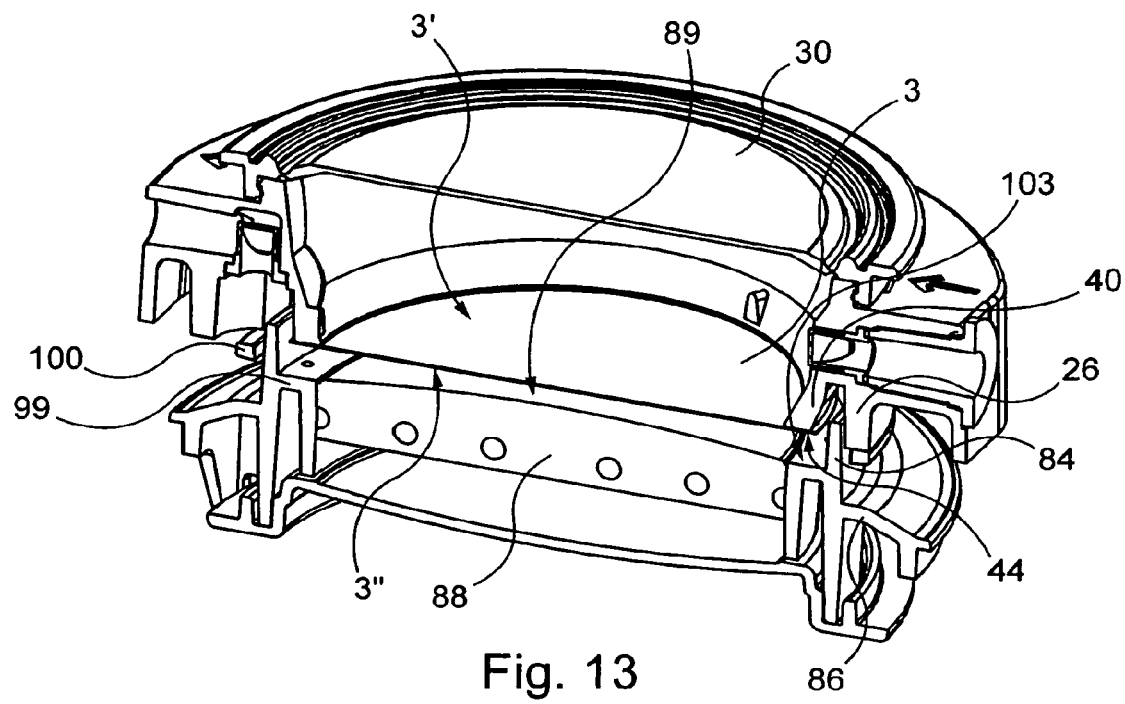
FIGS. 13 and 14 respectively are a sectioned perspective view and a side elevation view of this assembly in its intermediate centered position as illustrated in FIG. 10.
Figure 14:
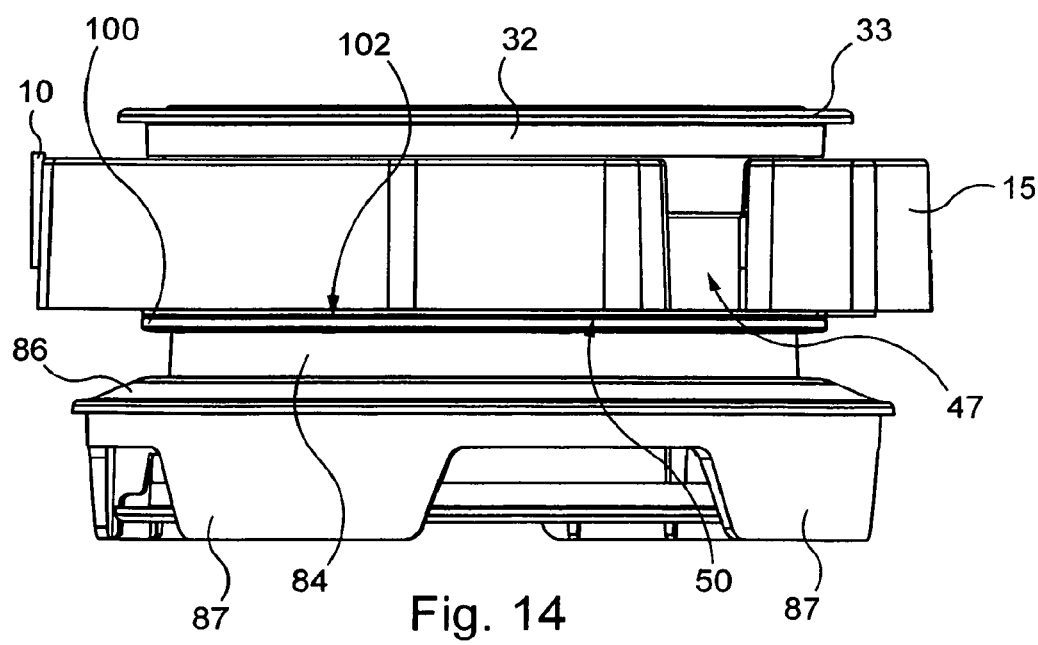

This engagement operation is continued until the wall 26 of the body of the filtration unit comes into abutment against the ring 100 of the cassette, the surface 50 of the wall 26 then being in contact with the surface 102 of the ring 100 as illustrated in FIGS. 10, 13 and 14.

The unit and the cassette are thus arranged in an intermediate position centered relative to one another and in which the membrane 3 is still spaced away from the gel growth medium with the surface 3" of this membrane facing the convex surface 89 of the gel growth medium, these being positioned concentrically relative to one another.

In this position, the operator then exerts a force to bring the unit and the cassette closer together, either by grasping this unit and this cassette between the thumb and the other fingers of one hand or by pressing this assembly against his hand and a fixed support.

Figure 11:
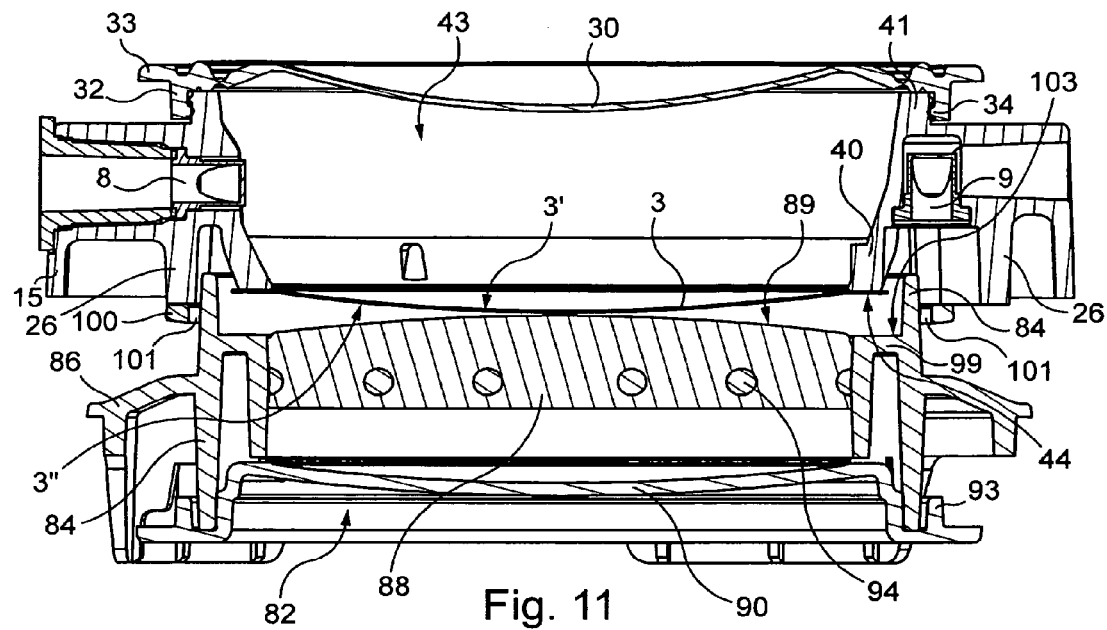

The operator exerts this force while pressing on the flexible lid 7 of the filtration unit so as to cause deformation of the wall 30, reducing the reception volume 43 as illustrated in FIG. 11.

Because the valve 8 and the wet membrane 3 enclose the volume 43 in a sealed manner (because of the bubble point phenomenon), reducing this reception volume 43 causes a slight rise in pressure.

In response to this rise in pressure, the membrane 3, held at its periphery against the surface 44, therefore adopts a slightly domed shape (its surface 3' becomes concave and surface 3" becomes convex) toward the outside of the unit (FIG. 11), the centers of the surfaces 3" and 89 thus moving closer to one another without, however, touching.

The operator continues and then increases the force with which he is bringing the unit and the cassette closer together until this force exceeds a predetermined threshold beyond which the frangible tabs 101 break.

It should be noted that the threshold at which the frangible tabs break and the flexibility of the lid are chosen in such a way as to cause enough deformation of the lid that this deformation allows enough of a raised pressure to be created in the chamber 43 to give the membrane the desired domed shape before this breaking threshold is reached.

When the force with which the items are brought closer together exceeds this predetermined threshold, the ring 100 is then released and slides along the wall 84 until it comes into abutment against the balcony 86. The stop that this ring forms is thus moved clear so that the body of the filtration unit then slides along the wall 84 of the cassette, with this wall 84 then engaged between the walls 26 and 40 of the filtration unit.

Figure 12:
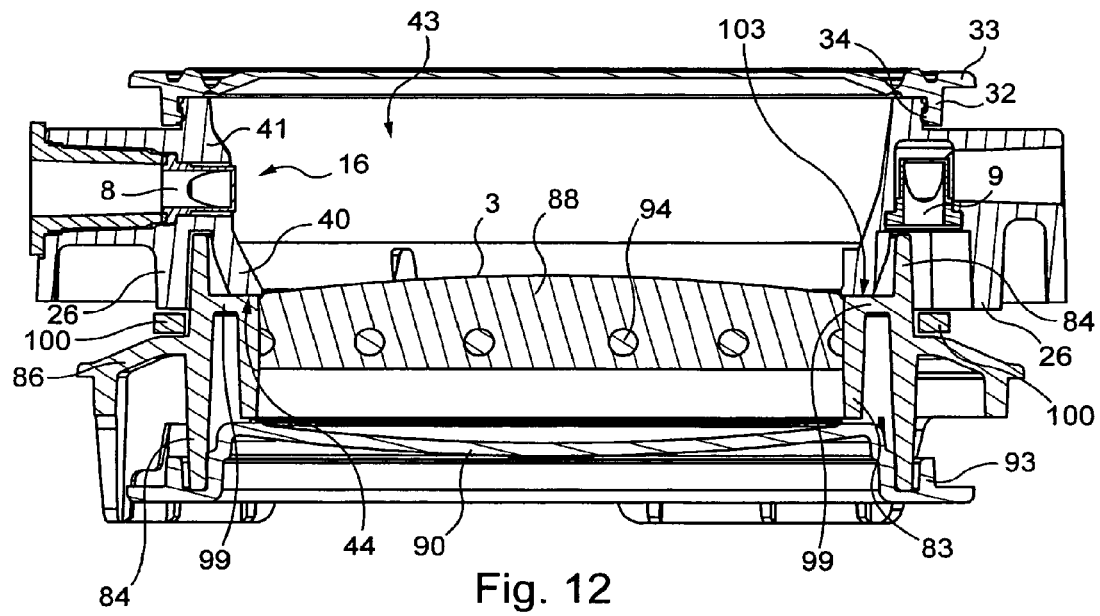

This engagement continues to the point where the unit and the cassette occupy their end-of-travel nested position in which the wall 40 of the unit butts against the wall 99 of the cassette, the surface 44 of the wall and the surface 103 of the wall 99 then being in contact with one another (FIG. 12).

During this step the surface 3″ of the membrane and the surface 89 of the gel growth medium gradually come into contact with one another, firstly via their center, then spreading out toward their periphery so as to drive the air toward the periphery in order to avoid the formation of air pockets between the membrane and the gel growth medium as such pockets could locally impede the growth of the micro-organisms (FIG. 12).

The sliding of the filtration unit once the stop 100 has been moved clear thus causes this unit to move from the intermediate position with respect to the cassette to the position in which it is nested within this cassette, the operation whereby the gel growth medium becomes covered by the membrane taking place quickly and effectively in a single action on the part of the operator.

In the nested position, the filtration unit is kept secured to the cassette by the facets 51 of the wall 26 which, by creating a local deformation of this wall, allow the wall 84 of the cassette to be nested between the wall 26 and the wall 40 of the unit so that the unit and the cassette cannot be detached from one another without the need to exert a substantial force in order to separate them.

This assembly is then incubated in an incubation chamber for long enough to grow the micro-organisms held in the membrane 3 so that they become visible and can be counted.

Several assemblies can be stacked on top of one another in the incubation chamber to facilitate storage.

The assemblies can also be inverted in order to limit the condensation forming on the gel growth medium.

In order to count the colonies once incubation is complete, it is possible either to remove the lid 7 and count the colonies directly or, if this lid is transparent, to count these colonies through this lid.

The use of frangible tabs 101 makes it possible to ensure from one unit to another, good repeatability of the predetermined threshold force that has to be exerted in order to cause the ring 100 to move clear, this ring 100 constituting a tamper indicator for the gel growth medium cassette, since the ring sits at a different height and is either mobile or non-mobile according to whether or not the cassette has already been used.

In an alternative form that has not been depicted, the stop able to move clear belongs not to a frangible ring but to elastically deformable teeth or ribs that may optionally, once the filtration unit has been slid, act as locking means (by latching for example) to lock the unit to the cassette in the nested position.

In yet another alternative form, the stop able to move clear is formed not on the gel growth medium cassette but on the filtration unit.

In yet another alternative form, the lid 7 of the unit is replaced by a non-detachable flexible wall (designed to be domed toward the membrane) or by a peelable film similar to the film 6.

The present invention is not restricted to the embodiment described and depicted but encompasses any alternative form of embodiment.

The invention claimed is:

1. A microbiological analysis method, comprising the steps of:
   selecting an analysis assembly comprising:
   a filtration unit and a gel growth medium cassette, said filtration unit comprising a filter membrane and a body with which said membrane is associated, said cassette comprising a body containing the said gel growth medium, the latter having a surface designed to be covered by said membrane, the body of the filtration unit and the body of the cassette are adapted to cooperate in order to occupy a nested position in which the membrane covers said surface of said gel growth medium, the body of said unit and the body of said cassette each being equipped with an intermediate stop, when said stops are in contact with one another, the filtration unit and the gel growth medium cassette are in an intermediate position in which said membrane is spaced away from said gel growth medium, said intermediate stop of said body of said cassette comprising a ring connected to said body of said cassette by frangible tabs;
   engaging said unit on said cassette until the intermediate stop of the body of said unit comes into contact with the intermediate stop of the body of said cassette; and
   breaking said frangible tabs causing said ring to move clear so as to allow said unit to move from said intermediate position into said nested position.

2. The method according to claim 1, wherein a unit comprising a flexible wall closing a chamber further bounded by a wall of the body of the filtration unit and by said membrane is selected as said filtration unit, and wherein breaking said frangible tabs causing said ring to move clear comprises a step of exerting a force to bring said unit and said cassette closer together that is above a predetermined threshold, by pressing on said flexible wall of said unit.

3. The method according to claim 2, wherein a wall adapted to deform under a force that is lower than a force required to move clear said stop is selected as said flexible wall.

4. The method according to claim 1, comprising, prior to the step of engaging said unit on said cassette, performing a sampling step and, subsequent to breaking said frangible tabs causing said ring to move clear, performing a step of growing micro-organisms collected on said membrane during said sampling step.

5. The method according to claim 4, wherein said sampling step comprises the steps of:
   selecting a filtration unit which comprises a peelable film;
   filtering a predetermined volume of liquid through said unit; and
   peeling said film.

* * * * *